US011593602B1

(12) United States Patent
Bricks

(10) Patent No.: US 11,593,602 B1
(45) Date of Patent: Feb. 28, 2023

(54) LABELING SYSTEM AND METHOD

(71) Applicant: Ipsum Diagnostics LLC, Atlanta, GA (US)

(72) Inventor: Lauren Bricks, Atlanta, GA (US)

(73) Assignee: Ipsum Diagnostics LLC, Atlanta, GA (US)

( * ) Notice: Subject to any disclaimer, the term of this patent is extended or adjusted under 35 U.S.C. 154(b) by 0 days.

(21) Appl. No.: 17/398,176

(22) Filed: Aug. 10, 2021

Related U.S. Application Data

(60) Provisional application No. 63/063,459, filed on Aug. 10, 2020.

(51) Int. Cl.
*G06K 19/06* (2006.01)
*G06K 7/14* (2006.01)
*B01L 3/00* (2006.01)

(52) U.S. Cl.
CPC ........ *G06K 19/06037* (2013.01); *B01L 3/545* (2013.01); *G06K 7/1413* (2013.01); *G06K 7/1417* (2013.01); *B01L 2300/021* (2013.01)

(58) Field of Classification Search
CPC ........ G06K 19/00; G06K 19/04; G06K 19/06; G06K 19/06037; G06K 7/1413; G06K 7/1417
USPC ...... 235/494, 487, 375, 462.01, 462.09, 454
See application file for complete search history.

(56) References Cited

U.S. PATENT DOCUMENTS

| | | | | |
|---|---|---|---|---|
| 6,158,779 A | * | 12/2000 | Petrick | B42D 15/00 283/79 |
| 2005/0075152 A1 | * | 4/2005 | Buck | B42D 5/025 462/64 |
| 2008/0121688 A1 | * | 5/2008 | Harrop | G06K 19/06046 235/494 |
| 2009/0289448 A1 | * | 11/2009 | Sample | B01L 3/5457 283/67 |
| 2011/0281346 A1 | * | 11/2011 | Halpern | B01L 9/54 435/307.1 |
| 2019/0362416 A1 | * | 11/2019 | Pesch | G06Q 30/08 |

* cited by examiner

*Primary Examiner* — Edwyn Labaze
(74) *Attorney, Agent, or Firm* — Smith Tempel Blaha LLC; Michael J. Tempel

(57) ABSTRACT

An adhesive-backed label having a plurality of adhesive-backed label portions, each of the adhesive-backed label portions comprising an instance of an identifying indicia, whereby one or more of the plurality of adhesive-backed label portions is applied to at least one collected sample so that the identifying indicia on the adhesive-backed label portion on the collected sample corresponds to the identifying indicia on at least one of the adhesive-backed label portions that remains on the adhesive-backed label, at least one of the adhesive-backed label portions on the adhesive-backed label also comprising a field configured to receive additional identifying indicia.

18 Claims, 8 Drawing Sheets

LABELING SYSTEM AND METHOD

RELATED APPLICATIONS

This application claims priority to and the benefit of U.S. Provisional Patent Application No. 63/063,459, entitled "LABELING SYSTEM AND METHOD," filed Aug. 10, 2020, the contents of which are hereby incorporated herein by reference in their entirety as if fully set forth below and for all applicable purposes.

FIELD

The present disclosure relates generally to labeling systems, and more specifically to a labeling system to track laboratory samples and other shipments.

BACKGROUND

When collecting and transferring medical samples and specimens for testing there are a number of challenges for maintaining integrity of the collected specimen, particularly specimens that are sent to a laboratory for testing (clinical, research, forensic testing, etc.). Current methods used for labeling specimens, verifying specimen identification information, maintaining chain of custody, maintaining supply requirements, handling variation in specimen quantities and types, and providing required documentation have many limitations and are prone to allowing errors.

A testing and diagnostic laboratory typically uses paper requisition forms with integrated labels, where the labels are used to associate the test order on the requisition form with the actual specimen. These forms cannot be photocopied or remotely printed because of the integrated labels, multicopy format, and a printed unique identifier (ID). Paper requisition forms with integrated labels are rigid and impose constraints that can prevent accurate specimen collection and testing. For example, paper templates cannot be changed on demand to accommodate different specimen collection and testing parameters, and possible depletion or shortage of specialized paper can cause delays in the ability to collect specimens. Moreover, paper requisition forms can require special printers that often must be ordered in advance.

Therefore, it would be desirable to have a way to simplify sample ordering and provide integrity in medical sample tracking thereby eliminating the shortcomings of current medical sample ordering and tracking systems.

SUMMARY

Various implementations of systems, methods and devices within the scope of the appended claims each have several aspects, no single one of which is solely responsible for the desirable attributes described herein. Without limiting the scope of the appended claims, some prominent features are described herein.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

One aspect of the disclosure provides a labeling system comprising an adhesive-backed label having a plurality of adhesive-backed label portions, each of the adhesive-backed label portions comprising an instance of an identifying indicia, whereby one or more of the plurality of adhesive-backed label portions is applied to at least one collected sample so that the identifying indicia on the adhesive-backed label portion on the collected sample corresponds to the identifying indicia on at least one of the adhesive-backed label portions that remains on the adhesive-backed label, at least one of the adhesive-backed label portions on the adhesive-backed label also comprising a field configured to receive additional identifying indicia.

Another aspect of the disclosure provides a method for labeling and tracking a medical sample including applying to a vessel in which a medical sample is contained an adhesive-backed label portion of a label having the patient's name and on which identifying indicia may be pre-printed; prior to shipping to a testing laboratory, scanning the identifying indicia on the adhesive-backed label portion for entry into an electronic portal and integrated laboratory information management system (LIMS); after receipt by a testing laboratory, scanning the identifying indicia on the adhesive-backed label portion; comparing the identifying indicia scanned and entered into the electronic portal prior to shipping to the testing laboratory to the identifying indicia scanned at the testing laboratory; and determining whether the identifying indicia scanned and entered into the electronic portal prior to shipping to the testing laboratory matches the identifying indicia scanned at the testing laboratory.

Another aspect of the disclosure provides a method for transport container labeling and tracking including applying to a transport container containing medical samples for delivery to a testing laboratory an adhesive-backed label portion of a label having identifying indicia pre-printed thereon; prior to shipping the transport container to the testing laboratory, scanning the identifying indicia on the adhesive-backed label portion for entry into an electronic portal and integrated LIMS; after receipt of the transport container by the testing laboratory, scanning the identifying indicia on the adhesive-backed label portion; comparing the identifying indicia scanned and entered into the electronic portal prior to shipping the transport container to the testing laboratory to the identifying indicia scanned after receipt of the transport container by testing laboratory; and determining whether the identifying indicia scanned and entered into the electronic portal prior to shipping the transport container to the testing laboratory matches the identifying indicia scanned at the testing laboratory.

BRIEF DESCRIPTION OF THE DRAWINGS

In the figures, like reference numerals refer to like parts throughout the various views unless otherwise indicated. For reference numerals with letter character designations such as "102a" or "102b", the letter character designations may differentiate two like parts or elements present in the same figure. Letter character designations for reference numerals may be omitted when it is intended that a reference numeral encompass all parts having the same reference numeral in all figures.

DETAILED DESCRIPTION

Figure 1:
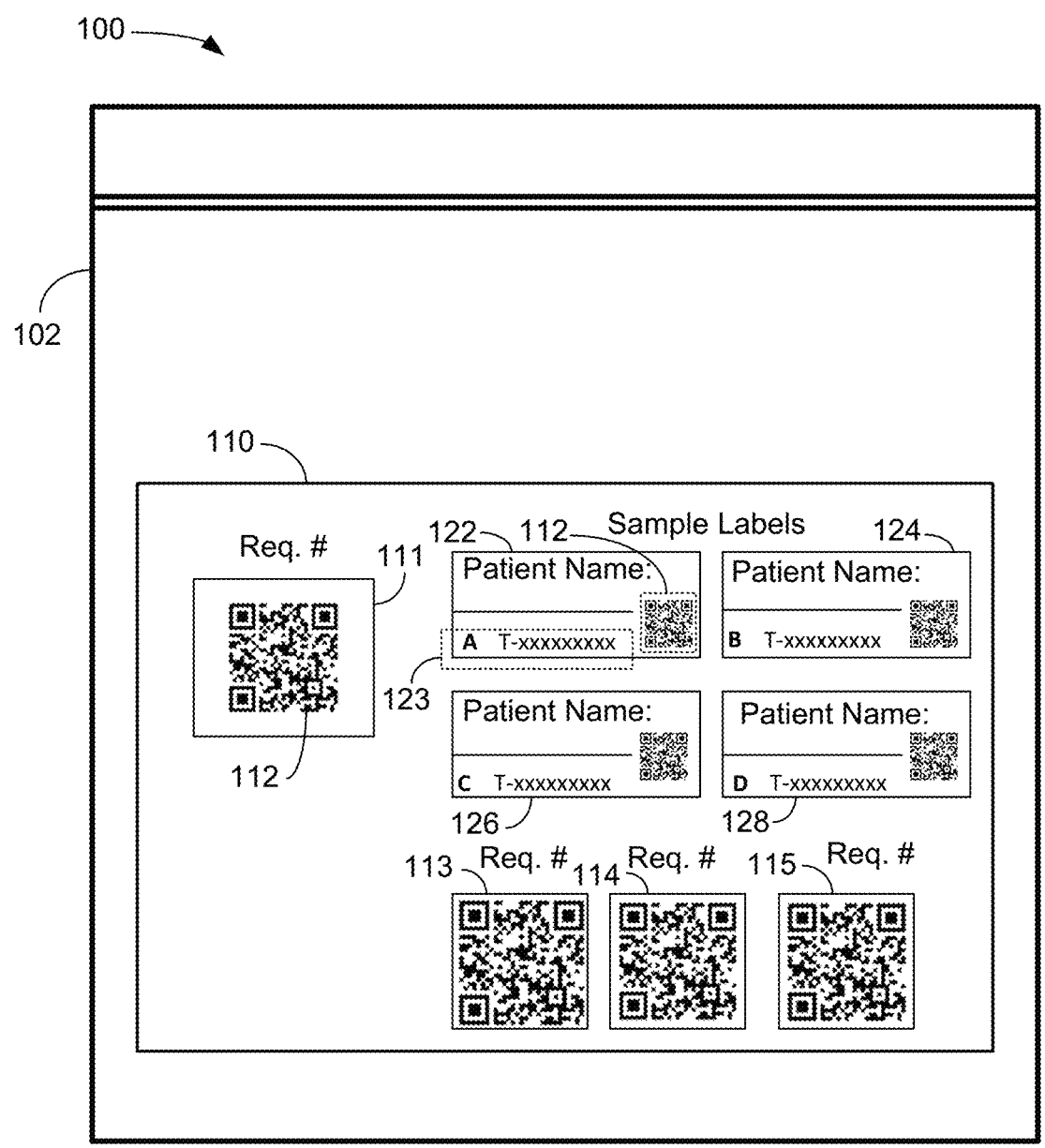
FIG. 1 is a diagram showing a medical sample collection system and labeling system.

The word "exemplary" is used herein to mean "serving as an example, instance, or illustration." Any aspect described herein as "exemplary" is not necessarily to be construed as preferred or advantageous over other aspects.

As used herein, the term "sample" and "specimen" may be used to describe a medical sample or medical specimen collected from a donor.

There are two primary methods for ordering medical specimens, electronically and on a traditional paper requisition form. A paper requisition form has integrated labels with a unique ID, often barcoded for scanning and typed for human readability. When orders are placed electronically, a printed copy of the order is used that often does not have integrated labels.

The lack of an integrated label on the requisition form with an electronically placed order creates limited options for labeling and tracking a sample. The label may be already affixed to the specimen tube, vial, bag, etc. The labels can be provided separately, but then must be affixed to the tube, vial, bag or other vessel. Barcode or other specialty indicia label printers can be costly, require information technology (IT) support, may require inventory such as blank labels, and may not work properly with some computers.

There is also an option to use paper requisition forms with independently printed labels, which cause other drawbacks including, but not limited to, a requirement for a printer capable of printing labels, mismatching labels with requisition forms and requirements to maintain a supply of blank labels.

These prior methods of labeling and tracking introduce higher instances of specimens not having acceptable labeling. Further, a sample collection vessel is often tube-shaped, and it is difficult to write on a tube, which increases instances of illegible handwriting possibly leading to sample labeling errors. Labels included in a collection kit or provided as part of supplies may be missed or separated from the collection supplies, increasing the rates of unlabeled specimens. Due to these challenges, information required (by hand or printed) on the labels is often missing, resulting in rejected specimens and/or delayed analysis reports.

In an exemplary embodiment, a labeling and tracking solution in accordance with exemplary embodiments of the disclosure dramatically increases the quality of laboratory testing. An exemplary embodiment of the disclosure provides improved labeling and tracking of specimens, simplifies the information needed for verification of identification of a specimen, provides full flexibility for paper or electronic test ordering, reduces specimen rejections caused by unlabeled samples to less than 1% and offers a solution for addressing systems that require more than one different barcoded ID number.

Additionally, the labeling and tracking solution described herein can be quickly and easily adapted for a wide range of applications. The system and method have the flexibility to accommodate collections of more than one sample, collections involving different specimen types and test selections specific for a specimen. Additionally, the system and method can be customized according to the needs of specific providers, such as designing labels to include unique identifiers generated by a provider's electronic medical record software and assigning specimens the next available requisition number in a provider's system.

Exemplary embodiments of the disclosure are directed to a labeling system that removes the need for those involved in specimen collection, labeling, tracking, etc., to rely on traditional paper requisition forms for processing orders.

Exemplary embodiments of the disclosure are directed to systems and methods that simplify sample ordering and provide integrity in medical sample tracking through an integrated labeling system comprising labels and label portions with the capability of adhering to any container type that in turn can be used to link corresponding sets of medical sample containers, transport containers, paperwork, etc. for purposes of positive identification, thereby eliminating the shortcomings of current medical sample ordering and tracking systems.

Figure 2:
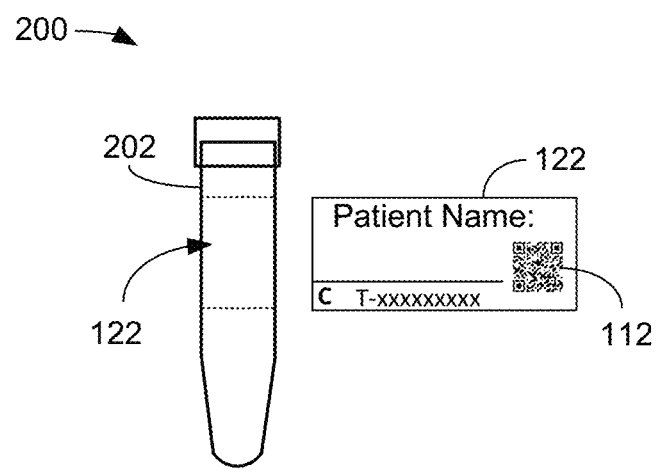
FIG. 2 is a diagram showing a sample collection vessel and a label of FIG. 1.
Figure 3:
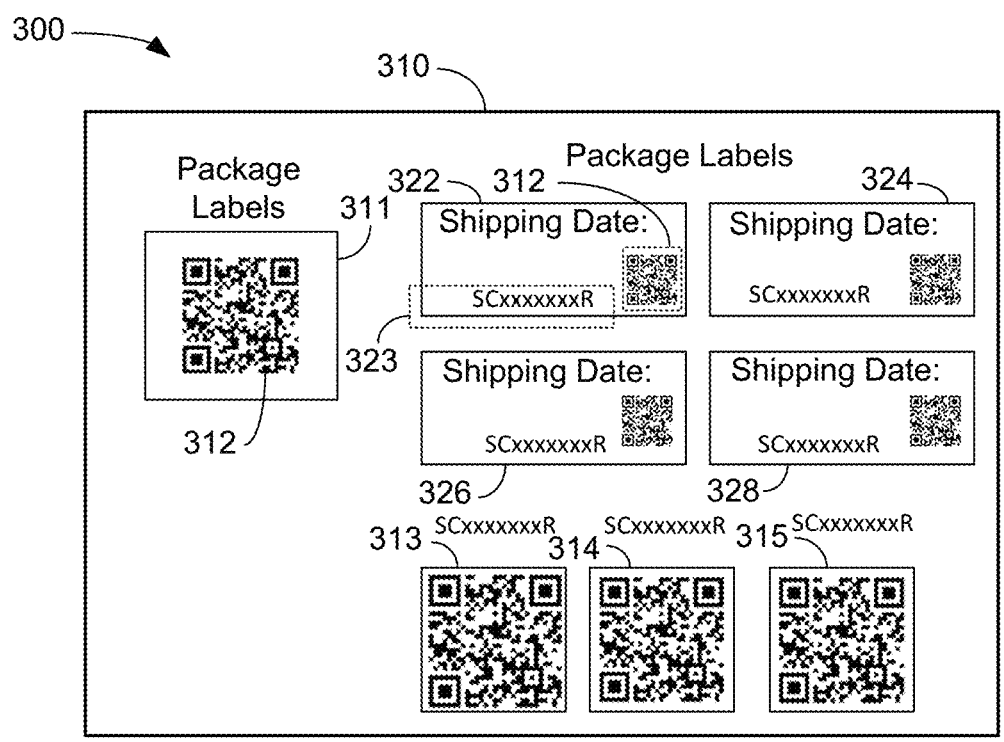
FIG. 3 is a drawing showing an alternative exemplary embodiment of a label of FIG. 1.
Figure 4:
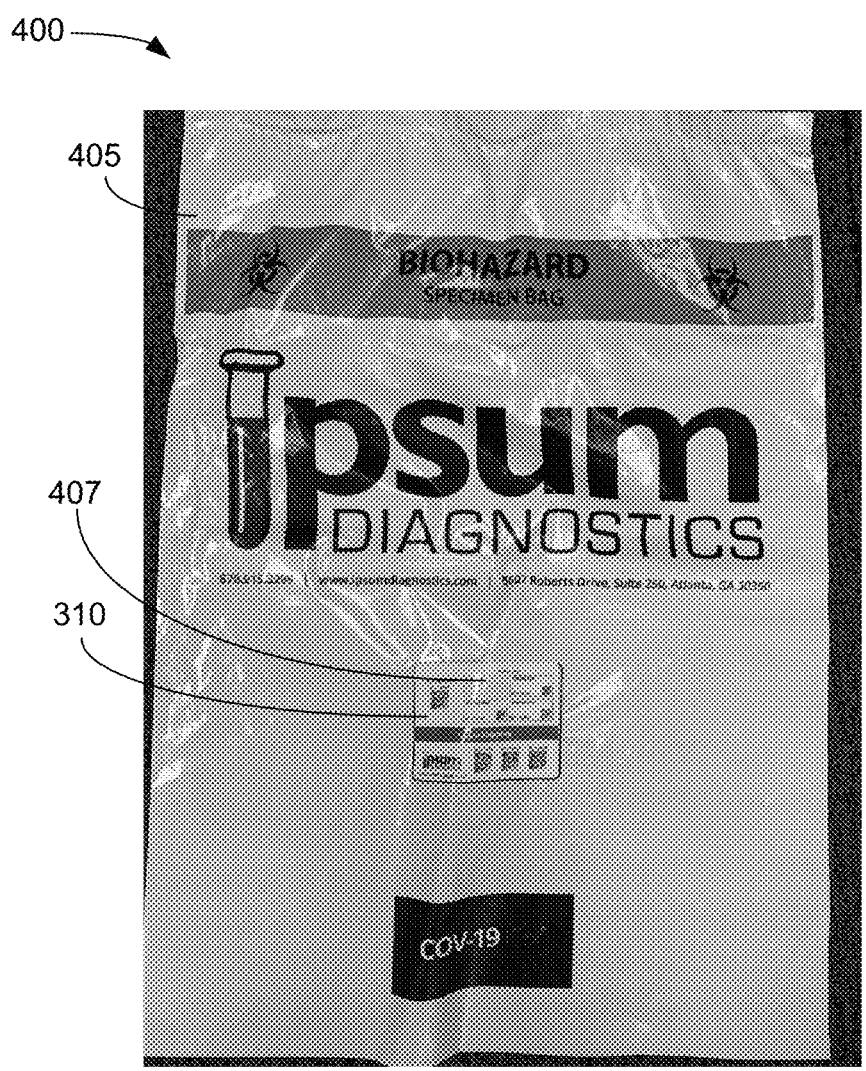
FIG. 4 is a diagram showing a transport container containing medical samples and a label of FIG. 3.
Figure 5:
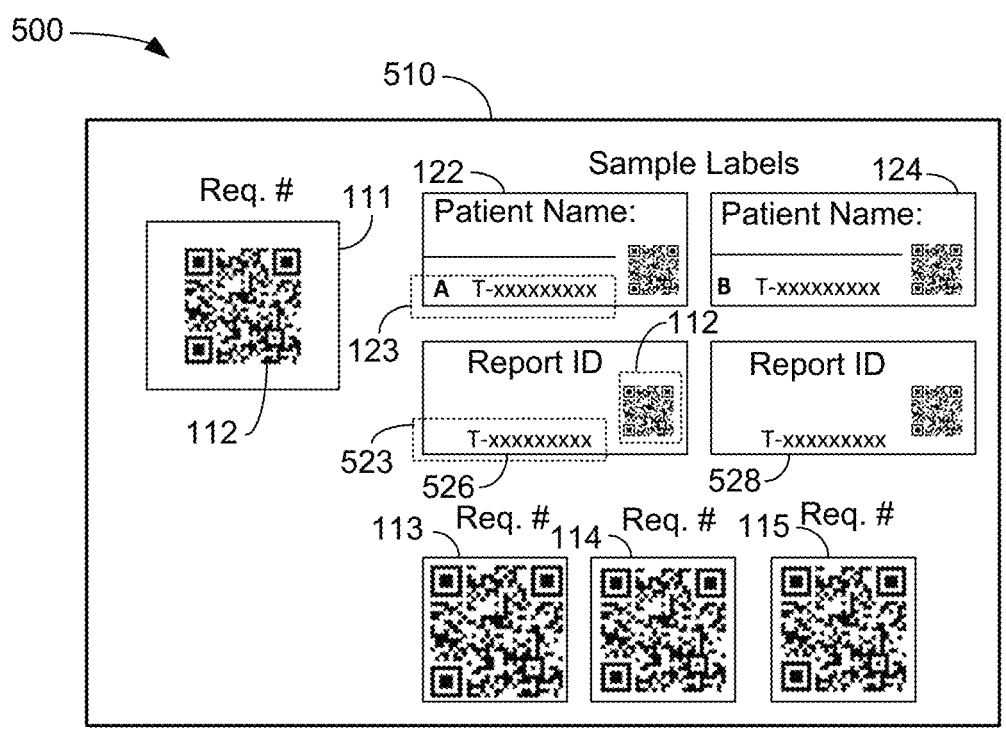
FIG. 5 is a drawing showing another alternative exemplary embodiment of a label of FIG. 1.
Figure 6:
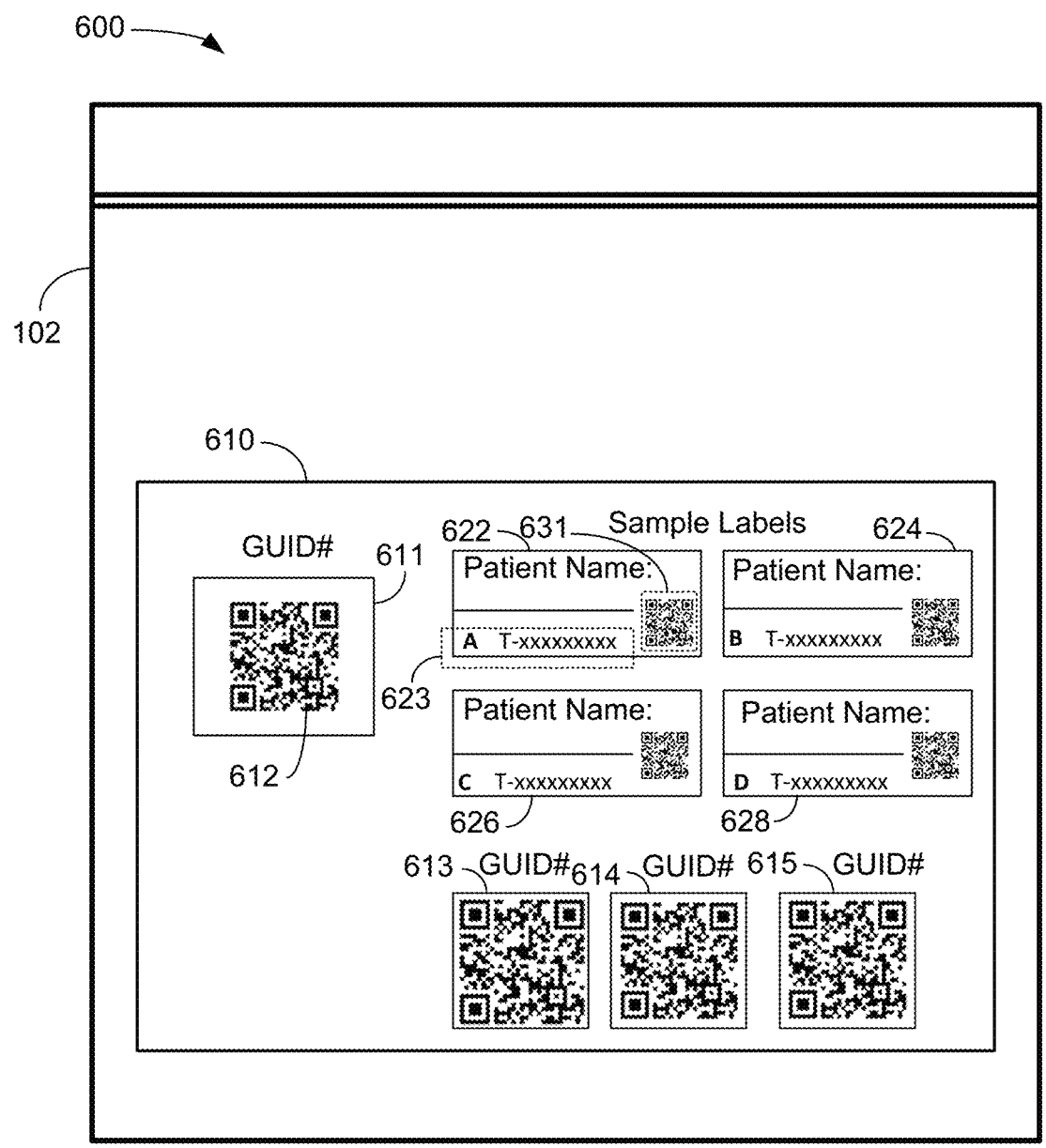
FIG. 6 is a drawing showing another alternative exemplary embodiment of a label of FIG. 1.

FIG. 1 is a diagram 100 showing a medical sample collection system and labeling system. FIG. 2 is a diagram 200 showing a sample collection vessel and a label of FIG. 1. FIG. 3, FIG. 5 and FIG. 6 are drawings showing alternative exemplary embodiments of the label of FIG. 1. FIG. 4 is a drawing showing a transport container containing medical samples and a label of FIG. 3.

Referring to FIG. 1 through FIG. 6, a container 102 includes a label 110. In an exemplary embodiment, the container 102 may be a plastic bag having a reusable closable feature, and may be interchangeably referred to as a "specimen bag," a "biohazard bag", a "specimen biohazard bag," etc.

In an exemplary embodiment, the label 110 may include unique identifying indicia, such as a QR code, a 2-D code, a barcode, or another unique identifying indicia that can be visually readable, electronically readable, or both visually and electronically readable. In the example shown, the identifying indicia is a QR code. In the example shown, the label 110 may be adhesive-backed and may comprise an adhesive-backed label portion 111 having identifying indicia, such as for example, a QR code 112 pre-printed thereon. The adhesive-backed label portion 111 having the QR code 112 may be a removable adhesive-backed label portion of the label 110 such that the label portion 111 having the QR code 112 can be removed from the label 110 and adhesively applied elsewhere. The identifying indicia, in this example the QR code 112, is repeated on other adhesive-backed label portions, such as label portions 113, 114, 115. The information contained in the QR code 112 is identical on the adhesive-backed label portions 111, 113, 114 and 115. In an exemplary embodiment, although three adhesive-backed label portions 113, 114 and 115 are shown in addition to the adhesive-backed label portion 111, any number of adhesive-backed label portions can be implemented.

The label 110 also comprises a number of adhesive-backed label portions 122, 124, 126 and 128. Each of the adhesive-backed label portions 122, 124, 126 and 128 may also include identical instances of the QR code 112. In an exemplary embodiment, the adhesive-backed label portions 122, 124, 126 and 128 may also include a place for the individual performing the specimen collection to write additional information related to the individual providing the specimen. For example, the name of the individual providing the specimen may be written on one or more of the adhesive-backed label portions 122, 124, 126 and 128. In an exemplary embodiment, the name of the individual providing the specimen may be written on one or more of the adhesive-backed label portions 122, 124, 126 and 128 prior to the adhesive-backed label portion being affixed to the sample collection vessel.

In an exemplary embodiment, the adhesive-backed label portions 122, 124, 126 and 128 may also include identifying indicia in addition to the QR code 112. For example, the adhesive-backed label portions 122, 124, 126 and 128 may include an alphanumeric character 123 (dotted line shown only on adhesive-backed label portion 122, for ease of illustration) that corresponds to the information in the QR code 112, such that an individual performing the specimen collection may enter such alphanumeric character into a tracking system instead of scanning the QR code 112, if needed. A tracking system may comprise a laboratory information management system (LIMS), or another electronic tracking system, that may be accessed through a portal or other electronic communication means. In an exemplary embodiment, although four adhesive-backed label portions 122, 124, 126 and 128 are shown on the label 110, any number of adhesive-backed label portions can be implemented.

In an exemplary embodiment, the unique label 110, which is affixed to container 102 before container 102 is delivered to a provider, serves as a very obvious visual cue to the individual performing the specimen collection and reinforces accurate labeling as the individual performing the specimen collection places the collected specimen into the container 102.

In an exemplary embodiment, the label 110 is unique due to the identifying indicia (the QR code 112 and the alphanumeric character 123) and can be individually tailored for different providers of specimen collection and testing services.

In an exemplary embodiment, the adhesive-backed label portions 111, 113, 114, 115, 122, 124, 126 and 128 are integrated with the label 110 and not separately provided, thus minimizing the likelihood that the labels may be misplaced, or otherwise disassociated from the specimen.

In an exemplary embodiment, the adhesive-backed label portions 122, 124, 126 and 128 facilitate the collection, tracking and maintenance of chain of custody of more than one specimen and different specimen types from a single specimen provider.

In an exemplary embodiment, the labeling system includes a "requisition label" with a unique ID that is uniquely coded, such as the QR code 112. In this exemplary embodiment, the adhesive-backed label portion 111 would be removed from the label 110 and affixed to the paper requisition form.

In an exemplary embodiment, the labeling system described herein allows the flexibility to use paper sample requisition forms, which can be easily photocopied and printed on any standard printer. Forms can be edited on demand to add test modality options, modify addresses, add provider information, etc. Forms do not have to be mailed or supplied to providers in advance.

In an exemplary embodiment, due to the corresponding identifying indicia on the collected sample (for example, one of the adhesive-backed label portions of the label 110 having the QR code 112, and placed on a sample collection vessel) and test order (electronic or paper), only one other identifier is required. Regulatory compliance requires two pieces of information to be present on the specimen label. In an exemplary embodiment, a donor's name can be handwritten on one of the adhesive-backed label portions 122, 124, 126 and 128, and together with the pre-printed unique identifier 112 provides the required two pieces of information per specimen. The pre-printed unique identifiers reduce the number of noncompliant samples, thereby reducing rejection of the sample or a sample being placed on hold due to not having the second identifier written or typed on the label.

In an exemplary embodiment, the labeling system described herein reduces the number of incorrect identifiers that may be introduced due to errors when transcribing identifiers (transposed numbers, misspelled names, etc.).

In an exemplary embodiment, when entering electronic test orders, QR or barcode scanners can be used but are not required. The unique ID can be scanned or hand typed.

In an exemplary embodiment, the labeling system described herein includes multiple specimen labels (adhesive-backed label portions 122, 124, 126 and 128 for example) that contain the coded ID (QR code 112) that can be scanned or human read (alphanumeric character 123) for typed entry.

In an exemplary embodiment, the labeling system and method described herein offers customization that is currently not available with other laboratory software or labeling systems, including the flexibility to accommodate collections of more than one sample, collections involving different specimen types and test selections specific for a specimen. Traditionally, such collections and specifications would require multiple electronic or paper test orders. Exemplary embodiments of the labeling system described here are completely flexible to accommodate these scenarios. For instance, labels can be modified to incorporate alphanumeric identifiers that correspond to different samples or specimen types.

In an exemplary embodiment, the labeling system described herein has complete flexibility if systems require more than one unique ID. Likewise, the labeling system can be used to distinguish clients based on any set of alphanumeric codes. The labeling system can include any length or combination of alphanumeric codes and special characters.

The labeling system is a customizable template, and can be used to print any text and logos, as well as provide extra labels that can be used for purposes such as, for example, client records or a patient copy (for example, a report ID (see FIG. 5, adhesive-backed label portions 526 and 528) for an electronic portal in which the patent may access information relating to the sample.

Multiple copies of the adhesive-backed label portion having the unique identifying indicia facilitate the replacement of a damaged label (such as a torn or unscannable QR code or indicia).

The labels can be designed and printed to have the physical properties to facilitate specimen transport and storage. For instance, the labels can be prepared to withstand condensation, heat and cold storage, and such that ink used to write a patient's name or other information on the label does not smear.

The size, placement and number of adhesive-backed label portions on a label can be modified and customized. For instance, labels can be printed in a smaller size to fit on smaller specimen tubes.

The labeling system can also be used for tracking shipments of specimens in any type of transport container (e.g., a package, bag, or other container). In an exemplary embodiment, as shown in FIG. 3, a label 310 includes transport container labels, readable as alphanumeric and by QR code, on adhesive-backed label portions 311, 313, 314, 315, 322, 324, 326 and 328. Each of the adhesive-backed label portions 311, 313, 314 and 315 may comprise identifying indicia, such as a QR code 312. Each of the adhesive-backed label portions 322, 324, 326 and 328 may comprise identifying indicia, such as a QR code 312 and alphanumeric character 323 (dotted line shown only on adhesive-backed label portion 322 for ease of illustration). In an exemplary embodiment, a provider can record the shipping date on adhesive-backed label portions 322, 324, 326 and 328.

Referring to FIG. 4, the label 310 may be placed on a transport container 405. For example, a transport container 405 may contain one or more containers 102 containing specimens for delivery to a testing laboratory, and any of the adhesive-backed label portions can be retained by the provider for records. For example, the location 407 on the label 310 depicts where an adhesive-backed label portion, such as adhesive-backed label portion 322 (FIG. 3), was removed and retained. Any of the transport container labels may be scanned by QR code or the alphanumeric character hand typed for entry of the transport container into a shipment module.

A shipping courier can scan the shipment by transport container label; likewise, the courier can retain a copy of the label for documentation.

The transport container 405 may be scanned by transport container label when received at a testing laboratory. Reconciliation for transport containers that have been sent and received can be performed.

Additionally, specimen bags, such as containers 102, contained within a transport container, such as transport container 405, can be scanned by a provider for entry into a shipment module under the corresponding transport container. Specimen bags may be scanned when received at the testing laboratory. Reconciliation for specimen bags that have been sent and received can be performed.

The labeling system as disclosed herein provides a true "paperless" test ordering solution. Because paper is a known source of pathogen transmission, removing the need for paper test orders (requisition forms) is significant for laboratories performing molecular testing, particularly for the COVID-19 virus. This applies to any contagious pathogen of which COVID-19 is a current high-profile example.

In an exemplary embodiment, an electronic portal may be implemented for entering test orders. The labeling system has a unique barcoded ID, which is either scanned or hand typed by the healthcare provider collecting the specimen. The test order is completed in an order management portal.

FIG. 2 is a diagram 200 showing a sample collection vessel 202 and an adhesive-backed label portion 122 of FIG. 1. In an exemplary embodiment, as medical sample may be collected and placed inside of the vessel 202. At the time just prior to sample collection, the individual collecting the sample would write the patient's name on the adhesive-backed label portion 122 in the space provided, remove the adhesive-backed label portion 122 from the label 110 of FIG. 1 (adhesive-backed label portion 122 shown in FIG. 2 for convenience only, any adhesive-backed label portion of the label 110 may be used), and apply the adhesive-backed label portion 122 to the vessel 202 and then place the collected sample inside the vessel 202. In this manner, the sample in the vessel 202 is identified to the donor of the sample using the unique identifying indicia (the QR code 112) on the adhesive-backed label portion 122 and the patient's name written on the adhesive-backed label portion 122.

FIG. 3 is a drawing showing an alternative exemplary embodiment of a label of FIG. 1. The label 310 in FIG. 3 is similar to the label 110 in FIG. 1; however, the label 310 includes adhesive-backed label portions 312, 313, 314, 315, 322, 324, 326 and 328 that may be used for transport container tracking as described herein.

FIG. 4 is a diagram 400 showing a transport container 405 containing specimens and a label 310 (FIG. 3). In an exemplary embodiment, the label 310 may be placed on the outside of the transport container 405. A provider can record the shipping date on one or more of adhesive-backed label portions 322, 324, 326 and 328. Before providing the transport container 405 to a courier service for delivery to a testing laboratory, the provider may scan any of the transport container labels for entry into a shipment module. Upon receipt of the transport container at the testing laboratory, any of the transport container labels may be scanned. Reconciliation for transport containers that have been sent and received can be performed.

FIG. 5 is a drawing showing an alternative exemplary embodiment of a label of FIG. 1. The label 510 in FIG. 4 is similar to the label 110 in FIG. 1; however, the label 510 includes adhesive-backed label portions 526 and 528 that may be used as a patient copy for access to an electronic portal in which the patient may access information relating to the sample. In the example shown in FIG. 5, the adhesive-backed label portions 526 and 528 also include instances of the QR code 112 and an alphanumeric character 523 (dotted line shown only on adhesive-backed label portion 526, for ease of illustration) that corresponds to the information in the QR code 112.

FIG. 6 is a drawing 600 showing an alternative exemplary embodiment of a label of FIG. 1. The label 610 in FIG. 6 is similar to the label 110 in FIG. 1; however, the label 610 comprises a QR code 612 in adhesive-backed label portion 611, and repeated in adhesive-backed label portions 613, 614 and 615, that represents a unique identifier, which may be generated by a healthcare provider's electronic medical record software. In the exemplary embodiment shown in FIG. 6, the adhesive-backed label portions 622, 624, 626 and 628 may also include identifying indicia. For example, the adhesive-backed label portions 622, 624, 626 and 628 may include identifying indicia, such as a QR code 631 and an alphanumeric character 623 (dotted lines shown only on adhesive-backed label portion 622, for ease of illustration) that corresponds to the QR code 631. In this example, the QR code 631 is distinct from, but is pre-programmed to correspond to, the information in the QR code 612. For example, in the example shown in FIG. 6, the QR code 612 may be different than the QR code 631, but the QR code 612 and the QR code 631 may be pre-programmed to correspond to each other.

Figure 7:
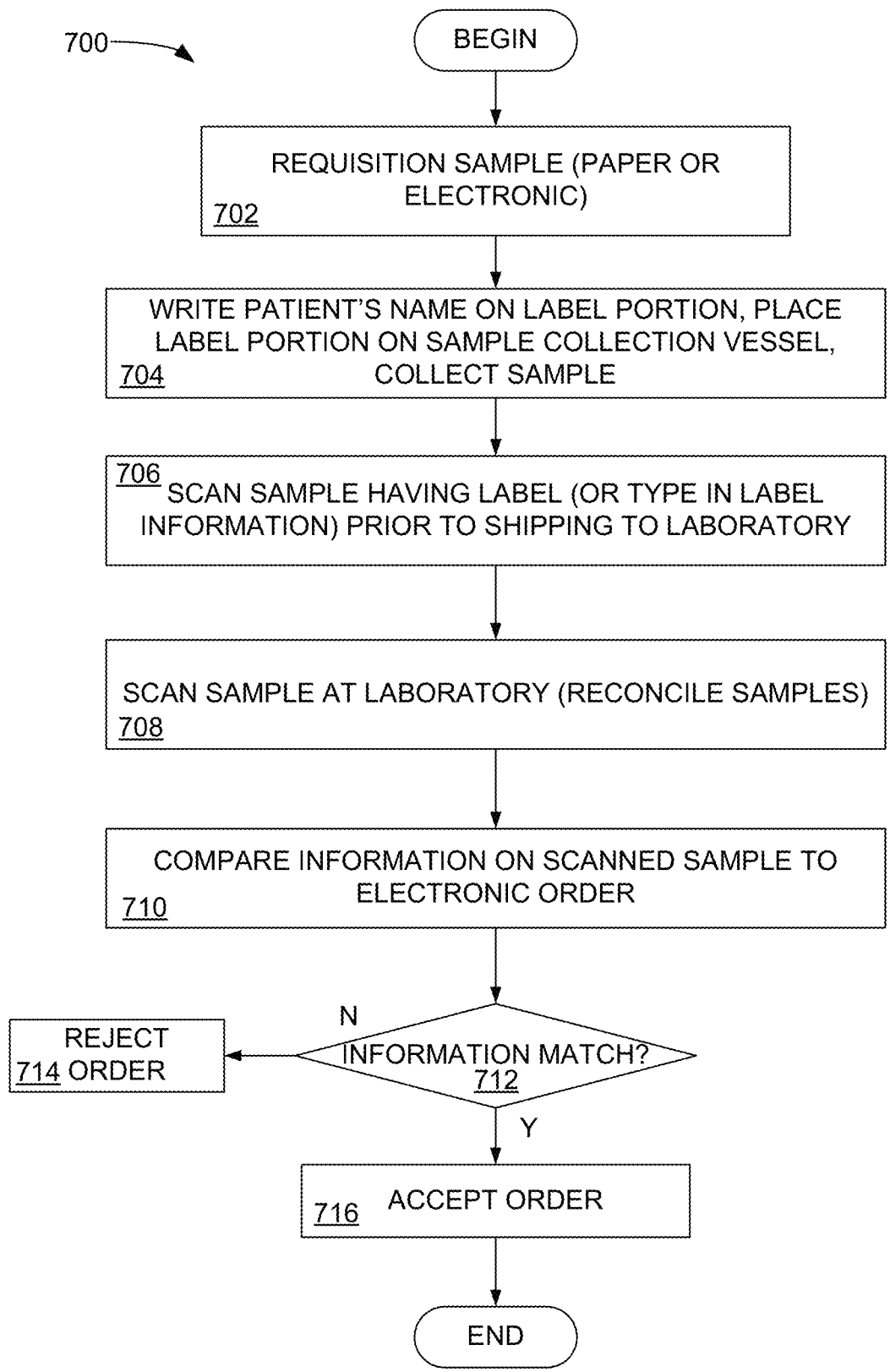
FIG. 7 is a drawing showing an exemplary method for sample tracking.

FIG. 7 is a drawing showing an example of the operation of a method 700 for sample tracking. The blocks in the method 700 can be performed in or out of the order shown, and in some embodiments, can be performed at least in part in parallel.

In block 702 a requisition for a medical sample is created. The requisition may be in the form of a paper requisition form or may be an electronic requisition.

In block 704, a patient's name may be written directly on an adhesive-backed label portion on which identifying indicia may be pre-printed, the adhesive-backed label portion may be applied directly to a sample collection vessel and the sample placed in the sample collection vessel.

In block 706, the identifying indicia on the adhesive-backed label portion, identifying the sample, may be scanned prior to shipping to a testing laboratory. For example, the identifying indicia may be scanned and entered into a LIMS via an electronic portal.

In block 708, the identifying indicia on the adhesive-backed label portion, identifying the sample, may be scanned upon arrival at the testing laboratory. For example, the identifying indicia may be scanned and entered into a LIMS via an electronic portal.

In block 710, the information scanned at the sample collection location (block 506) may be compared to the information scanned at the testing laboratory (block 708).

In block 712, it is determined whether the information scanned at the sample collection location (block 706) matches the information scanned at the testing laboratory (block 710).

If it is determined at block 712 that the information scanned at the sample collection location does not match the information scanned at the testing laboratory, then the sample is rejected in block 714.

If it is determined at block 712 that the information scanned at the sample collection location matches the information scanned at the testing laboratory, then the sample is accepted in block 716.

Figure 8:
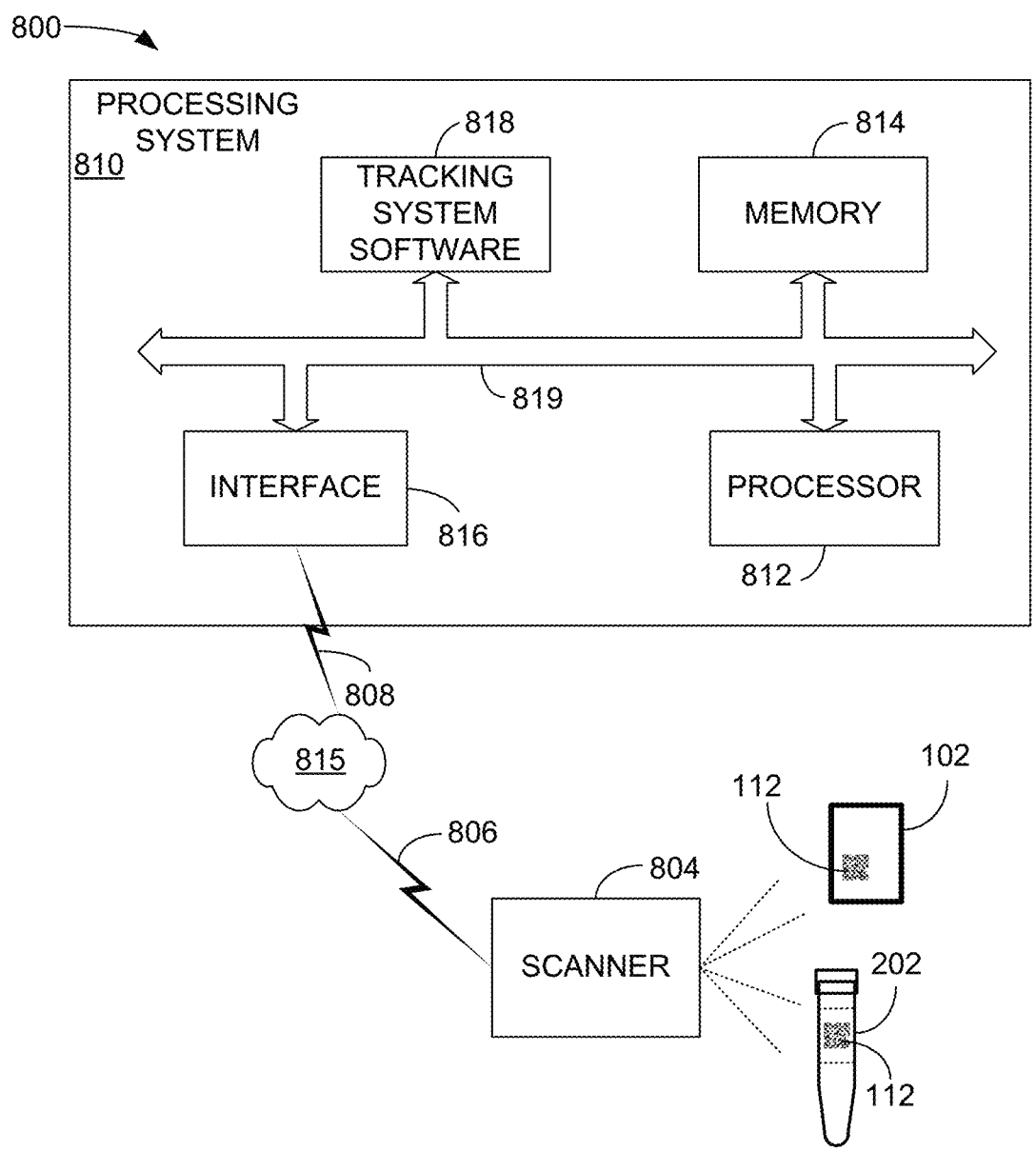
FIG. 8 is a diagram of a sample tracking system.

FIG. 8 is a diagram 800 of a sample tracking system. In an exemplary embodiment, the system 800 includes a processing system 810, a scanner 804 and a network 815. In an exemplary embodiment, the processing system 810 may include a processor 812, a memory 814, an interface 816 and a tracking system software module 818, operatively coupled together over a system bus 819.

The memory 814 may be configured to store data and program code, and may generally comprise analog and/or digital processing elements. The processor 812 and the memory 814 may cooperate to control, configure, program, or otherwise fully or partially control some or all of the operation of the embodiments of the tracking system described herein. In an exemplary embodiment, the memory 814 may be configured, or be configurable, to execute one or more portions of the tracking system software module 818.

A scanner 804 may be coupled to a network 815 over a wired or wireless connection 806. The interface 816 may also be coupled to the network 815 over a wired or wireless connection 808. Connections 806 and 808 are illustrated as wireless connections for simplicity of illustration. The network 815 may be any communication network or connection and may comprise wired and wireless elements.

In an exemplary embodiment, a medical sample may be collected and placed in a collection vessel 202 on which one of the adhesive-backed label portions having identifying indicia may be placed, or a collection of medical samples may be placed in a transport container 405 to which a label 310 containing transport container labels is affixed. The QR code 112 (or any other identifying indicia) may be scanned by the scanner 804 and the information relating to the QR code transmitted through the network 815 for receipt by the interface 816. In an alternative exemplary embodiment, QR code 112 (or any other identifying indicia) on a container 102, or any other transport container (such as transport container 405), may be scanned by the scanner 804 and the information relating to the QR code 112 (or other identifying indicia) transmitted through the network 815 for receipt by the interface 816 and processing system 810 for processing as described herein.

The information in the QR code 112 is then processed by the tracking system software module 818, the processor 812 and the memory 814 to collect the information associated with the QR code 112, 312 and/or 612, or any of the identifying indicia described herein. In an exemplary embodiment, some or all of the processing system 810 and scanner 804 may be implemented at one or more locations that may be separate from each other. The processor 812, memory 814, tracking system software 818 and interface 816 may be implemented in a single location as shown in FIG. 8, or portions of the elements of the processing system 810 may be implemented separately or disparately, but configured to interoperate.

In an exemplary embodiment, the processing system 810, network 815 and scanner 804 may comprise some or all of an electronic portal described herein, and may comprise some or all of a LIMS as described herein.

An apparatus implementing the system and method described herein may be a stand-alone device or may be part of a larger device. A device may be (i) a stand-alone integrated circuit (IC), (ii) a set of one or more ICs that may include memory ICs for storing data and/or instructions, (iii) an RFIC such as an RF receiver (RPR) or an RF transmitter/receiver (RTR), (iv) an ASIC such as a mobile station modem (MSM), (v) a module that may be embedded within other devices, (vi) a receiver, cellular phone, wireless device, handset, or mobile unit, (vii) etc.

As used in this description, the terms "component," "database," "module," "system," and the like are intended to refer to a computer-related entity, either hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device may be a component. One or more components may reside within a process and/or thread of execution, and a component may be localized on one computer and/or distributed between two or more computers. In addition, these components may execute from various computer readable media having various data structures stored thereon. The components may communicate by way of local and/or remote processes such as in accordance with a signal having one or more data packets (e.g., data from one component interacting with another component in a local system, distributed system, and/or across a network such as the Internet with other systems by way of the signal).

Although selected aspects have been illustrated and described in detail, it will be understood that various substitutions and alterations may be made therein without departing from the spirit and scope of the present invention, as defined by the following claims.

What is claimed is:

1. A labeling system, comprising:
    an adhesive-backed label having a plurality of adhesive-backed label portions, each of the adhesive-backed label portions comprising an instance of an identifying indicia, whereby one or more of the plurality of adhesive-backed label portions is applied to at least one collected sample so that the identifying indicia on the adhesive-backed label portion on the collected sample corresponds to the identifying indicia on at least one of the adhesive-backed label portions that remains on the adhesive-backed label, at least one of the adhesive-backed label portions on the adhesive-backed label also comprising a field configured to receive additional identifying indicia, wherein the identifying indicia comprises a unique identifier generated by a provider's electronic medical record software and wherein the unique identifier comprises a first QR code and a second QR code, the second QR code being distinct from the first QR code, the second QR code being pre-programmed to correspond to the first QR code.

2. The labeling system of claim 1, wherein the identifying indicia comprises at least one of a QR code, a barcode, and/or another unique identifier.

3. The labeling system of claim 1, wherein at least some of the adhesive-backed label portions comprise an alphanumeric identifier that corresponds to the identifying indicia.

4. The labeling system of claim 1, wherein the additional identifying indicia comprises information corresponding to a donor of the sample.

5. The labeling system of claim 1, further comprising a processing system having a processor and a memory configured to receive and store information associated with the identifying indicia.

6. The labeling system of claim 1, wherein the plurality of adhesive-backed label portions are used as a patient copy for access to an electronic portal in which the patient may access information relating to the at least one collected sample.

7. A method for labeling and tracking a medical sample, comprising:
   applying to a vessel in which a medical sample is contained, an adhesive-backed label portion of a label having the patient's name and on which identifying indicia may be pre-printed, the identifying indicia comprising a unique identifier generated by a provider's electronic medical record software and wherein the unique identifier comprises a first QR code and a second QR code, the second QR code being distinct from the first QR code, the second QR code being pre-programmed to correspond to the first QR code;
   prior to shipping to a testing laboratory, scanning the identifying indicia on the adhesive-backed label portion for entry into an electronic portal and integrated laboratory information management system;
   after receipt by a testing laboratory, scanning the identifying indicia on the adhesive-backed label portion;
   comparing the identifying indicia scanned and entered into the electronic portal prior to shipping to the testing laboratory to the identifying indicia scanned at the testing laboratory; and
   determining whether the identifying indicia scanned and entered into the electronic portal prior to shipping to the testing laboratory matches the identifying indicia scanned at the testing laboratory.

8. The method of claim 7, wherein the identifying indicia comprises at least one of a QR code, a barcode, and/or another unique identifier.

9. The method of claim 7, wherein the adhesive-backed label portion further comprises an alphanumeric identifier that corresponds to the identifying indicia.

10. The method of claim 7, further comprising adding additional identifying indicia to the adhesive-backed label portion on the adhesive-backed label, wherein the additional identifying indicia comprises information corresponding to a donor of the sample.

11. The method of claim 7, further comprising storing information associated with the identifying indicia.

12. The method of claim 7, wherein the adhesive-backed label portion is used as a patient copy for access to an electronic portal in which the patient may access information relating to the at least one collected sample.

13. A method for transport container labeling and tracking, comprising:
   applying to a transport container containing medical samples for delivery to a testing laboratory, an adhesive-backed label portion of a label having identifying indicia pre-printed thereon, the identifying indicia comprising a unique identifier generated by a provider's electronic medical record software and wherein the unique identifier comprises a first QR code and a second QR code, the second QR code being distinct from the first QR code, the second QR code being pre-programmed to correspond to the first QR code;
   prior to shipping the transport container to the testing laboratory, scanning the identifying indicia on the adhesive-backed label portion for entry into an electronic portal and integrated laboratory information management system;
   after receipt of the transport container by the testing laboratory, scanning the identifying indicia on the adhesive-backed label portion;
   comparing the identifying indicia scanned and entered into the electronic portal prior to shipping the transport container to the testing laboratory to the identifying indicia scanned after receipt of the transport container by testing laboratory; and
   determining whether the identifying indicia scanned and entered into the electronic portal prior to shipping the transport container to the testing laboratory matches the identifying indicia scanned at the testing laboratory.

14. The method of claim 13, wherein the identifying indicia comprises at least one of a QR code, a barcode, and/or another unique identifier.

15. The method of claim 13, wherein the adhesive-backed label portion further comprises an alphanumeric identifier that corresponds to the identifying indicia.

16. The method of claim 13, further comprising adding additional identifying indicia to the adhesive-backed label portion on the adhesive-backed label, wherein the additional identifying indicia comprises information corresponding to a donor of the sample.

17. The method of claim 13, further comprising storing information associated with the identifying indicia.

18. The method of claim 13, wherein the adhesive-backed label portion is used as a patient copy for access to an electronic portal in which the patient may access information relating to the at least one collected sample.

* * * * *